(12) United States Patent
Giordano

(10) Patent No.: US 9,410,179 B2
(45) Date of Patent: Aug. 9, 2016

(54) **DIAGNOSTIC METHOD FOR THE DETERMINATION OF *HELICOBACTER PYLORI***

(75) Inventor: Paolo Giordano, Salerno (IT)

(73) Assignee: ABS ADVANCED BIOMEDICAL SYSTEMS SRL, Cernusco sul Naviglio, Milan (IT)

( * ) Notice: Subject to any disclaimer, the term of this patent is extended or adjusted under 35 U.S.C. 154(b) by 1033 days.

(21) Appl. No.: 12/529,528

(22) PCT Filed: Mar. 7, 2008

(86) PCT No.: PCT/IT2008/000153
§ 371 (c)(1),
(2), (4) Date: Sep. 1, 2009

(87) PCT Pub. No.: WO2008/111104
PCT Pub. Date: Sep. 18, 2008

(65) Prior Publication Data
US 2010/0047833 A1    Feb. 25, 2010

(30) Foreign Application Priority Data
Mar. 13, 2007   (EP) .................................... 07425143

(51) Int. Cl.
*C12Q 1/58*    (2006.01)
*C12Q 1/04*    (2006.01)

(52) U.S. Cl.
CPC . *C12Q 1/04* (2013.01); *C12Q 1/045* (2013.01)

(58) Field of Classification Search
CPC .......................................................... C12Q 1/04
USPC ............................................................ 435/12
See application file for complete search history.

(56) References Cited

U.S. PATENT DOCUMENTS

| | | |
|---|---|---|
| 4,672,078 A | 6/1987 | Sakai et al. |
| 4,748,113 A | 5/1988 | Marshall |
| 5,439,801 A | 8/1995 | Jackson |
| 7,008,777 B2 | 3/2006 | Marshall et al. |
| 2003/0077680 A1* | 4/2003 | Marshall et al. ............... 435/12 |
| 2004/0033963 A1* | 2/2004 | Yu et al. ........................ 514/23 |

OTHER PUBLICATIONS

Mobley et al., Characterization of Urease from Campylobacter pylori, Journal of Clinical Microbiology, 1988, p. 831-836.*
PCT International Search Report for PCT/IT2008/000153 filed on Mar. 7, 2008 in the name of ABS Advanced Biomedical Systems s.r.l.
PCT Written Opinion for PCT/IT2008/000153 filed on Mar. 7, 2008 in the name of ABS Advanced Biomedical Systems s.r.l.

* cited by examiner

*Primary Examiner* — Taeyoon Kim
*Assistant Examiner* — Tiffany Gough
(74) *Attorney, Agent, or Firm* — Robert E. Alderson, Jr.

(57) ABSTRACT

The present invention relates to a diagnostic method for the determination of *Helicobacter pylori* in a tissue biopsy comprising the step of incubating a tissue biopsy with an aqueous diagnostic reagent comprising urea and a pH indicator, and determining any pH change, characterized in that said diagnostic reagent comprises a lactone, and that the ratio between the volume of the reagent and the volume of the sample is variable and less than 30.

22 Claims, No Drawings

DIAGNOSTIC METHOD FOR THE DETERMINATION OF *HELICOBACTER PYLORI*

CROSS REFERENCE TO RELATED APPLICATIONS

The present application is the US national stage of International Application PCT/IT2008/000153 filed on Mar. 7, 2008 which, in turn, claims priority to European Application 07425143.0, filed on Mar. 13, 2007.

The present invention relates to a method and a diagnostic kit for the determination of *Helicobacter pylori* in tissue biopsies.

*Helicobacter pylori* is an infectious agent which is the causative agent of gastric and duodenal ulcers and since 1994, has also been included in the list of carcinogenic agents.

At present, the eradication of *Helicobacter pylori* is possible by means of pharmacological agents, ensuring a success rate of 96%.

Diagnosis of *H. pylori* infection may be performed by means of various methods, including a breath test, testing for the presence of the bacteria in faeces, and analysis of a biopsy sample. Although the first two methods are considered by some authors to be the tests of reference for the diagnosis of *H. pylori* infection in the gastric mucosa, detection of the presence of the bacterium in biopsy tissue is still considered an accurate, sensitive and specific method, particularly for patients undergoing endoscopic examination.

Assaying for the presence of the bacterium in tissue biopsy material may be performed by means of three different methods: histological examination, bacterial culture, and determination of the presence of urease. The latter test is based on the unusual capacity of *H. pylori* to produce high quantities of urease, an enzyme not produced by the human body.

It is exactly thanks to this particular characteristic that *Helicobacter pylori* is capable of colonising the gastric mucosa, despite the high acidity of gastric juice. Indeed, urease breaks down the urea present in the medium into $NH_3$ and $CO_2$ thus forming a microenvironment where the ammonium ions neutralise the hydrochloric acid in gastric juice and preventing the *Helicobacter pylori* from being destroyed.

Hence the presence of this enzyme in biopsy samples is highly indicative of the presence of *H. pylori*.

The procedures used in various different urease tests are essentially very similar: a biopsy sample is added to a medium which may be in either liquid, gel or dehydrated form. The medium contains urea, a pH indicator dye and a buffer. The presence of urease causes hydrolysis of the urea with the consequent production of ammonium ions and then an increase in the pH, sufficient to cause the development of the colour of the indicator dye.

The main advantage offered by the urease test is the possibility of diagnosing the presence or absence of infection in less time and in a simpler manner with respect to detection by means of histological methods or bacterial culture isolation.

However, the tests currently on the market have limits, both in terms of sensitivity and speed of execution. Indeed, certain commercially available tests suggest waiting up to 24 hours to judge whether the result is effectively negative. In particular, when the bacterial load is very low, such as in the case of patients with atrophic gastritis or who have recently undergone antibiotic treatment, the time necessary for the development of the colour may be hours. Indeed, the identification of a positive test is faster the greater the bacterial load present in the biopsy.

On the other hand, waiting for such long periods of time can also lead to false positive results due to the growth of bacteria capable of breaking down the urea in the biopsy sample.

This problem has been resolved in the known art by eliminating the use of buffer. Indeed, the absence of buffer causes an increase in the sensitivity and speed of execution of the test, and the development of the colour can be visible even within a minute, even though some publications in the literature recommend reading at 10 minutes.

Methods of this type ("one minute test") are described in the specific literature. However, in the solutions described, the reagent must be prepared at the time of use or used within 5 days at most, if stored in a refrigerator at 4° C. This is because the urea is unstable over time in the absence of a buffer system and tends to be broken down rapidly to give ammonia and carbon dioxide. Hence, if the buffer-free diagnostic reagent is not used immediately or stored in a refrigerator, false positives can be obtained during use due to the presence of ammonia resulting from the natural decomposition of the urea.

Consequently, if on the one hand, the absence of buffer agent increases the sensitivity and speed of the diagnostic method, on the other hand, it negatively influences the stability of the reagent, particularly the urea.

Hence, the problem addressed by the present invention is that of providing a diagnostic method for the determination of *Helicobacter pylori* in tissue biopsies, which is both rapid and has high sensitivity, but at the same time has prolonged stability over time and can potentially be stored at room temperature.

Said problem is resolved by a diagnostic method and a diagnostic kit as described in the appended claims.

The present invention relates to an improved diagnostic method for the detection of *Helicobacter pylori* urease activity in a tissue biopsy, preferably a gastric tissue biopsy.

The system comprises the use of a particular category of substances, known as lactones, capable of preventing the natural decomposition of the urea which acts as a substrate for the activity of the enzyme, and a pH indicator, such as for example phenol red.

The presence of lactone stabilises the urea but does not inhibit urease, if present, from breaking it down into $NH_3$ and $CO_2$. The ammonia will then cause a change in the pH of the diagnostic reagent and hence the development of the indicator.

It has surprisingly been found that lactone not only avoids degradation of the urea but does not influence the test outcome. Indeed, lactone achieves the correct balance between the necessary stabilisation of the urea over time and excessive stabilisation impeding its enzymatic degradation by urease.

The formulation allows the attainment of a solution which is stable over time at room temperature, even in the absence of buffer systems.

Examples of lactones that can be used in the method of the invention are selected from the group constituted by gamma-butyrolactone, beta-butyrolactone, gamma-thiobutyrolactone, 2-acetyl-gamma-butyrolactone, gamma-valerolactone, delta-valerolactone, gamma-octanoylactone and epsilon-caprolactone. The preferred lactone for use is gamma-valerolactone.

The concentration of the urea in the diagnostic reagent is comprised of between 5 and 100 g/L, preferably between 10 and 60 g/L, while the lactone is present in quantities between 1 and 150 mL/L, preferably between 3 and 100 mL/L.

The diagnostic reagent preferably also comprises a preservative agent, for example sodium azide.

The concentration of preservative agent is comprised of between 0.05% and 0.5% by weight, preferably between 0.07% and 0.2% by weight.

Thanks to the absence of buffer, the diagnostic method of the invention is capable of obtaining the maximum speed of detection of urease activity. For example, tests conducted on samples containing *Helicobacter pylori* caused diagnostic reagent colour development in times comprised of between 1 minute and 10 minutes, while negative samples have been observed for approx. 24 hours without showing any colour change. The sensitivity and specificity of determination of urease activity are both increased, and are equal to approx. 94% an approx. 100% respectively.

At the same time, the diagnostic method stabilises the urea and allows the diagnostic reagent to be stored at room temperature (25° C.) for periods of time in excess of 18 months.

In one preferred embodiment of the invention the above-mentioned rapidity of execution and the sensitivity of the method are obtained by using a variable diagnostic reagent/tissue biopsy ratio equal to 10-300 μL:1 mm$^3$, preferably equal to 10-30 μL:1 mm$^3$. Advantageously, the tissue biopsy has dimensions comprised of between 1 and 10 mm$^3$.

In particular, the stability of the reagent, also in the liquid phase, allows the creation of an analytical system in which the quantity of reagent can be variable and limited to the minimum necessary because the biopsy samples are completely immersed. This way a high concentration of ammonia in the medium is obtained, causing an increased rate of pH change and thus detection of urease activity. In other words, it has been verified that using the diagnostic reagent/biopsy ratio described above, an increase in test response rate is obtained which is greater than that which would result from the elimination of buffer alone, using fixed, predetermined reagent volumes.

While on the one hand, the lack of buffer system allows maximising the rate of pH change, on the other hand, it exposes the system to the risk of artefacts due to the presence of substances capable of modifying the pH of the solution on the biopsy sample. However, if that occurs, it is sufficient to add a further small quantity of reagent, so as to obtain a starting solution of the appropriate colour.

In practical use, the operator inserts the biopsy sample in a transparent container, preferably with a conical bottom, and then adds the diagnostic reagent by means of a dropper inserted in the reagent bottle, or any system capable of adding small quantities in sequence (a few μl at a time), until the biopsy is completely covered. Obviously, the container will have sufficiently reduced dimensions so as to allow the sample to be covered with reagent while remaining within the above-described volume range of the latter. If the reagent changes colour immediately, this will very likely be an artefact due to the presence of basic substances in the biopsy sample. In this case, the operator adds reagent until obtaining the desired initial condition (yellow solution in the case of using phenol red as indicator).

In one particular embodiment of the invention, the diagnostic reagent can also comprise a buffer at a pH comprised of between 5.0 and 7.0, depending on the pH indicator used (for phenol red the optimal pH varies between 5.5 and 6.8). The buffers that can be used include sodium/potassium phosphate, sodium citrate, sodium acetate based buffers.

In one further embodiment, the present invention relates to a diagnostic kit for determining urease activity in a tissue biopsy sample comprising previously prepared, pre-measured and pre-packaged raw materials, as well as related sterile, non-sterile or sterilisable single-use materials, such as for example a conical bottomed container for the tissue biopsy, mixing vessels for the components and pipettes or droppers for adding the diagnostic reagent to the tissue sample.

Hence, said kit will comprise the enzyme substrate, i.e. urea, a lactone and a pH indicator in pre-measured quantities. The pre-measured components may be in separate packs or already mixed to give a single, ready to use, aqueous solution.

Optionally, the kit may also contain a preservative, for example sodium azide, itself also in pre-measured amounts.

In the case where the pre-measured components of the kit are in separate containers, once having opened the kit, the laboratory technician will only have to prepare the diagnostic reagent by mixing the pre-measured components, preferably previously dissolved in an appropriate quantity of deionised water. The reagent thus obtained will then be applied to the tissue biopsy, observing any colour change within a period of 1-10 minutes.

In the case where the kit components are already mixed in an aqueous ready-to-use solution, once the kit is open, the laboratory technician (using a pipette or dropper) will add the diagnostic reagent to the biopsy sample, which has been placed in a container, preferably with a conical bottom.

EXAMPLES 1 mm$^3$ gastric biopsy samples, taken from the antrum and floor of patients affected by duodenal or gastric ulcers, have been analysed.

The samples have been placed in a transparent, conical-bottomed container along with 30 μL of a diagnostic reagent, obtained by mixing the following components in the following concentrations, expressed per liter of ready to use reagent:
  20 g of urea;
  6.6 mL of γ-valerolactone;
  16.6 mg/L of phenol red;
  sodium azide, as preservative, at a final concentration of 0.09%.

The initial colour of the solution is standardised by adjusting the absorbance at 450 nm to a value of 0.85.

The positive samples caused the development of the colour of the solution in times comprised of between 1 minute and 10 minutes. Samples that were negative at 10 minutes have been observed for 24 hours, without showing any further colour change.

The sensitivity of the rapid test was 94%, while the specificity was 100%.

In order to evaluate the rate of colour change of the reagent, a study has been carried out in solution, by adding a predetermined quantity of urease, extracted from Canavalia ensiformis (Sigma Aldrich), to the same volume of the reagent of the invention and a commercial reagent (UFT-200, ABS Advanced Biomedical Systems Srl).

The development kinetics of the two reagents have been obtained by measuring the OD at 540 nm following the addition of urease (160 mU). The results obtained demonstrate that the development kinetics of the preparation of the invention reach 50% of the final value after 40 s, while the buffered solution reaches 50% of the plateau value after 200 s.

In order to determine the stability of the diagnostic reagent, several aliquots of the same have been stored in sealed glass vials at a temperature of 50° C., for a total period of 6 months. The development kinetics of the reagent, after the addition of urease (160 mU), have been determined at seven day intervals.

The results obtained show that the unbuffered reagent maintains its characteristics of sensitivity to urease for over 2.5 months, equivalent to stability of over 18 months at 25° C.

The invention claimed is:

1. A diagnostic method for detecting *Helicobacter pylori* in a tissue biopsy, the method comprising:
    incubating a tissue biopsy with an aqueous diagnostic reagent comprising urea, a lactone and a pH indicator wherein the incubating is performed for a period of 10 minutes or less; and
    determining a pH change in the aqueous diagnostic reagent.

2. The diagnostic method according to claim 1, wherein the diagnostic reagent/tissue biopsy ratio is equal to 10-300 µL:1 mm$^3$.

3. The diagnostic method according to claim 1, wherein said tissue biopsy has dimensions of between 0.1 and 10 mm$^3$.

4. The diagnostic method according to claim 1, wherein said urea is comprised in a quantity between 5 and 100 g/L, and said lactone is comprised in a quantity between 1 and 150 mL/L.

5. The diagnostic method according to claim 1, wherein said lactone is selected from the group consisting of gamma-butyrolactone, betabutyrolactone, gamma-thiobutyrolactone, 2-acetyl-gamma-butyrolactone, gamma-valerolactone, delta-valerolactone, gamma-octanoylactone and epsiloncaprolactone.

6. The diagnostic method according to claim 1, further comprising a preservative.

7. The diagnostic method according to claim 1, wherein said pH indicator is phenol red.

8. The diagnostic method according to claim 1, wherein the pH change is determined by measuring absorbance of a sample comprising the tissue biopsy and the aqueous diagnostic reagent at a wavelength selected for the pH indicator.

9. The diagnostic method according to claim 6, wherein the preservative is comprised at a concentration of between 0.05% and 0.5% by weight.

10. The diagnostic method according to claim 1, wherein said diagnostic reagent comprises a sodium acetate, sodium citrate or sodium/potassium phosphate buffer at a pH of between 5.0 and 6.8.

11. The diagnostic method according to claim 1, wherein said diagnostic reagent is stored at room temperature for at least 15 months.

12. The diagnostic method according to claim 1, wherein said tissue biopsy is a gastric tissue biopsy.

13. A diagnostic kit for detecting *Helicobacter pylori* in a tissue biopsy, the diagnostic kit comprising pre-measured quantities of: an enzyme substrate urea, a lactone, and a pH indicator in an already mixed, aqueous ready-to-use solution.

14. The diagnostic kit according to claim 13, further comprising a preservative.

15. The diagnostic kit according to claim 13 further comprising a sodium acetate, sodium citrate or sodium/potassium phosphate buffer at a pH of between 5.0 and 6.8.

16. The diagnostic kit according to claim 13 wherein the pre-measured quantities are comprised in single-use, sterile, non-sterile or sterilisable materials.

17. The diagnostic kit according to claim 16, wherein said material is selected from conical bottomed containers, pipettes and/or droppers.

18. The method of claim 1, wherein the diagnostic reagent/tissue biopsy ratio is equal to 10-30 µL:1 mm$^3$.

19. The method of claim 1, wherein said urea is between 10 and 60 g/L, and said lactone is between 3 and 100 mL/L.

20. The method of claim 1, wherein said lactone is gamma-valerolactone.

21. The method of claim 6, wherein the preservative is sodium azide.

22. The method of claim 6, wherein the concentration of preservative is between 0.07% and 0.2% by weight.

* * * * *